(12) United States Patent
Royal et al.

(10) Patent No.: US 9,399,012 B2
(45) Date of Patent: Jul. 26, 2016

(54) REDUCED DOSE INTRAVENOUS ACETAMINOPHEN

(75) Inventors: Mike Allan Royal, San Diego, CA (US); James Bradley Breitmeyer, Rancho Santa Fe, CA (US)

(73) Assignee: MALLINCKRODT IP, Dublin (IE)

( * ) Notice: Subject to any disclaimer, the term of this patent is extended or adjusted under 35 U.S.C. 154(b) by 1032 days.

(21) Appl. No.: 12/270,796

(22) Filed: Nov. 13, 2008

(65) Prior Publication Data

US 2009/0143474 A1 Jun. 4, 2009

Related U.S. Application Data

(60) Provisional application No. 60/987,761, filed on Nov. 13, 2007.

(51) Int. Cl.
*A61K 31/16* (2006.01)
*A61K 9/00* (2006.01)
*A61K 47/02* (2006.01)
*A61K 47/18* (2006.01)

(52) U.S. Cl.
CPC ............... *A61K 9/0019* (2013.01); *A61K 47/02* (2013.01); *A61K 47/18* (2013.01); *A61K 47/183* (2013.01)

(58) Field of Classification Search
USPC ......................................................... 514/629
See application file for complete search history.

(56) References Cited

U.S. PATENT DOCUMENTS

| | | | |
|---|---|---|---|
| 5,270,050 A | 12/1993 | Coquelet et al. | |
| 5,384,124 A * | 1/1995 | Courteille | A61K 9/1635 34/284 |
| 6,028,222 A * | 2/2000 | Dietlin et al. | 564/4 |
| 6,593,331 B2 | 7/2003 | Camborde et al. | |
| 6,992,218 B2 * | 1/2006 | Dietlin | A61K 9/0019 564/223 |
| 7,255,860 B2 * | 8/2007 | Shelton et al. | 424/145.1 |

FOREIGN PATENT DOCUMENTS

| | | |
|---|---|---|
| DE | 279405 | 6/1990 |
| GP | 870101510 | 12/1987 |
| JP | 1987-4229 | 1/1987 |
| JP | 1999-514013 | 11/1999 |
| JP | 2004-269363 | 9/2004 |
| JP | 2006-517544 | 7/2006 |
| KR | 1993-0011994 | 3/1993 |

OTHER PUBLICATIONS

Pettersson et al., Journal of cardiothoracic and Vascular Anesthesia, 2005;19(3):306-309.*
McNeil Labs Pharmacologist Review of NDA 17-785, Apr. 5, 1976.
PCT/US08/83458 Search Report dated Jan. 29, 2009.
JP 2010-534188 Office Action dated May 14, 2013.
Apotel Information Sheet, last revision Feb. 10, 1998, 2 pages.
Budavari, et al. , "The Merck Index, 12th Edition; 1996, p. 9—Acetaminophen."
Clements, et al."Data point weighting in pharmacokinetic analysis: intravenous paracetamol in man." J. Pharm. Pharmac., 1976, 28, p. 107-109.
Depre, et al. "Tolerance and Pharmacokinetics of Propacetamol, a paracetamol formulation for intravenous use." Fundam Clin Pharmacol (1992) 6, p. 259-262.
Fairbrother, "Acetaminophen." 1974, p. 1-109.
JP 2010-534188 office action mailed Feb. 4, 2014.
Rawlins, et al. "Pharmacokinetics of Paracetamol (Acetaminophen) after Intravenuous and Oral Administration." Europ. J. Clin. Pharmacol. 11, (1977), p. 283-286.
Summary Basis of Approval (SBA) for Injectapap (NDA 17-785), May 27, 1986, p. 1-35.
Yan, et al. "Study and Preparation of Paracetamol Solution for Injection." Pharmaceutical Bulletin 1986 21 (7), p. 387-389.
Exhibit A to the Declaration of Dr. Mike A. Royal: "A True and Correct Copy of the Crriculum Vitae of Dr. Mike A. Royal;" 15 pages.
Exhibit B to the Declaration of Dr. Mike A. Royal: Anderson et al.; "Acetaminophen Analgesia in Children: Placebo Effect and Pain Resolution After Tonsillectomy;" Eur. J. Clin. Pharmacol; vol. 57; pp. 559-569; 2001.
Exhibit C to the Declaration of Dr. Mike A. Royal: Wininger et al.; "A Randomized, Double-Blind, Placebo-Controlled, Multicenter, Repeat-Dose Study of Two Intravenous Acetaminophen Dosing Regimens for the Treatment of Pain After Abdominal Laparoscopic Surgery;" Clinical Therapeutics; vol. 32(14); pp. 2348-2369; 2010.
Exhibit D to the Declaration of Dr. Mike A. Royal: Candiotti et al.; "Safety of Multiple-Dose Intravenous Acetaminophen in Adult Inpatients;" Pain Medicine; vol. 11; pp. 1841-1848; 2010.
Exhibit E to the Declaration of Dr. Mike A. Royal: "McNeil's Background Package on Acetaminophen for the Nonprescription Drugs Advisory Committee;" Sep. 19, 2002; Downloaded Apr. 17, 2014; 75 pages. http://www.fda.gov/ohrms/dockets/ac /02/briefing/3882b1_13_mcneil-acetaminophen.htm.
Exhibit F to the Declaration of Dr. Mike A. Royal: Juhl et al.; "Analgesic Efficacy and Safety of Intravenous Paracetamol (Acetaminophen) Administered as a 2 g Starting Dose Following Third Molar Surgery;" European Journal of Pain; vol. 10; pp. 371-377; 2006.
Exhibit G to the Declaration of Dr. Mike A. Royal: Sinatra et al.; "Efficacy and Safety of Single and Repeated Administration of 1 Gram Intravenous Acetaminophen Injection (Paracetamol) for Pain Management after Major Orthopedic Surgery;" Anesthesiology; vol. 102(4); pp. 822-831; 2005.
Exhibit H to the Declaration of Dr. Mike A. Royal: Moller et al.; "Onset of Acetaminophen Analgesia: Comparison of Oral and Intravenous Routes After Third Molar Surgery;" British Journal of Anaesthesia; 94 (5); pp. 642-648; 2005.

(Continued)

*Primary Examiner* — San-Ming Hui
(74) *Attorney, Agent, or Firm* — Mayer Brown LLP

(57) ABSTRACT

Described herein are compositions and methods for intravenous administration of acetaminophen at a single dose level of less than about 1000 mg for the treatment or prevention of pain (e.g., postoperative pain) and/or fever.

109 Claims, No Drawings

(56) References Cited

OTHER PUBLICATIONS

Exhibit I to the Declaration of Dr. Mike A. Royal: Singla et al.; "Plasma and Cerebrospinal Fluid Pharmacokinetic Parameters After Single-Dose Administration of Intravenous, Oral, or Rectal Acetaminophen;" Pain Practice; vol. 12 (7); pp. 523-532; 2012.
Exhibit J to the Declaration of Dr. Mike A. Royal: OFIRMEV® Prescribing Information; Patient Insert; 2013; 12 pages.
Anand et al.; "Intravenous Acetaminophen vs. Ketorolac for Postoperative Analgesia After Ambulatory Parathyroidectomy;" Scandinavian Journal of Pain; vol. 4(4); pp. 249-253; 2013.
Atef et al.; "Intravenous Paracetamol is Highly Effective in Pain Treatment After Tonsillectomy in Adults;" Eur Arch Otorhinolaryngol; vol. 265(3); pp. 351-355; 2008.
Cadence Pharmaceuticals Annual Report; 2012; 128 pages.
Singla et al.; "A Phase III, Multi-Center, Open-Label, Prospective, Repeated Dose, Randomized, Controlled, Multi-Day Study of the Safety of Intravenous Acetaminophen in Adult Inpatients;" Poster Presentation; Presented at: 34th Annual Regional Anesthesia Meeting and Workshops; Apr. 30 to May 3, 2009; Phoenix, AZ.
Candiotti et al.; "Opioid Adjuvants for Multimodal Pain Management;" Anesthesiology News; pp. 1-8; 2011.
Marier et al.; "Application of Trial Simulations to Support Optimal Dosing of Intravenous Acetaminophen in Pediatric Patients: Regulatory Approval of the Product Based on a Minimum Number of Patients;" 1 page.
"Cadence Pharmaceuticals Estimates Fourth Quarter and Full Year 2013 Product Revenue and Provides Full Year 2014 Revenue Guidance;" The Wall Street Journal; Downloaded Jan. 18, 2104; 3 pages. http://online.wsj.com/article/PR-CO-20140113-905162.html.
Pacheco et al.; "The Role of Multimodal Analgesia in the Perioperative Setting; A Special Feature on OFIRMEV® (Acetaminophen) Injection;" 2013; 10 pages.
Schwartz et al.; "Intravenous Acetaminophen: An Alternative to Opioids for Pain Management?"; Hospital Pediatrics; vol. 3; pp. 294-296; 2013.
Susan Yudt; "Ofirmev® Use in Multi-Modal Pain Strategies;" California Association of Nurse Anesthetists, Spring Meeting; 2012; 22 pages.
Peacock et al.; "A Randomized Study of the Efficacy and Safety of Intravenous Acetaminophen Compared to Oral Acetaminophen for the Treatment of Fever;" Acad Emerg Med; vol. 18(4); 360-366; 2011.
Decision of Rejection for Japanese Patent Application No. 2010-534188; 3 pages.
English Translation of the Decision of Rejection for Japanese Patent Application No. 2010-534188; 1 page.
English Translation of Japanese Unexamined Patent Publication No. 2004-269363; 6 pages.
English Translation of Japanese Laid Open Patent Publication No. 2006-517544; 7 pages.
English Translation of Japanese Laid Open Patent Publication No. 1999-514013 (11-514013); 22 pages.
English Translation of EP Publication No. 0207193 corresponding to Japanese unexamined Patent Publication No. 1987-4229(62/4229); 7 pages.
Kumpulainen et al.; "Paracetamol (Acetaminophen) Penetrates Readily Into the Cerebrospinal Fluid of Children After Intravenous Administration;" Pediatrics; vol. 119(4); pp. 766-771; 2007.
Ameer et al.; "Absolute and Relative Bioavailability of Oral Acetaminophen Preparations;" Journal of Pharmaceutical Sciences; vol. 72(8); 955-958; 1983.
Oscier et al.; "Paracetamol—A Review of Three Routes of Administration;" Update in Anaesthesia; Edition 23; pp. 112-114; 2007.
Oscier et al.; "Intravenous Paracetamol: A Sensible Choice for Postoperative Analgesia?" Anaesthesia Points West; vol. 40(1); pp. 52-55; 2007.
Toms et al.; "Single Dose Oral Paracetamol (Acetaminophen) for Postoperative Pain in Adults (Review);" Cochrane Database of Systematic Reviews; 2008; Issue 4 (118 pages).
Tzortzopoulou et al.; "Single Dose Intravenous Propacetamol or Intravenous Paracetamol for Postoperative Pain (Review);" Cochrane Database of Systematic Reviews 2011; Issue 10 (136 pages).
Viscusi et al.; "IV Acetaminophen Improves Pain Management and Reduces Opioid Requirements in Surgical Patients: A Review of the Clinical Data and Case-Based Presentations;" McMahon Publishing; 2012 (8 pages).
Petring et al.; "Normal Postoperative Gastric Emptying After Orthopaedic Surgery With Spinal Anaesthesia and i.m. Ketorolac as the First Postoperative Analgesic;" British Journal of Anaesthesia; 74, pp. 257-260; 1995.
Barden et al.; "Single Dose Oral Propacetamol (Acetaminophen) for Postoperative Pain (Review);" Cochrane Database of Systematic Reviews 2004; Issue 1 (17 pages).
Berger et al.; "Intestinal Absorption in Patients After Cardiac Surgery;" Crit Care Med; vol. 28; No. 7; pp. 2217-2223; 2000.
Evaluatng Analgesa: the Challenges; Henry J. McQuary, Jayne E. Edwards, and R. Andrew Moore; American Journal of Therapeutics 9, 179-187 (2002).

* cited by examiner

REDUCED DOSE INTRAVENOUS ACETAMINOPHEN

CROSS-REFERENCE TO RELATED APPLICATIONS

This application is related to and claims priority to U.S. Provisional Patent Application No. 60/987,761, entitled "Reduced Dose Intravenous Acetaminophen" filed on Nov. 13, 2007, which is incorporated herein by reference in its entirety.

BACKGROUND OF THE INVENTION

In the hospital, particularly in the postoperative setting, pain is a primary concern of patients. Opioid analgesics have been used to treat postoperative pain since 1784 and parenteral morphine has been a primary treatment modality since the 1850s. While opioids are highly effective in the treatment of many painful conditions, they have side effects and dose-dependent risks including nausea, vomiting, constipation, urinary retention, sedation, and respiratory depression. Similarly, non steroidal anti-inflammatory drugs (NSAIDs), including the older non selective (dual inhibitor) products and newer cyclo-oxygenase (COX)-2 products, have a variety of unwanted side effects especially when used in the perioperative setting. Non selective NSAIDs are associated with platelet dysfunction and the potential for bleeding at the surgical site, upper gastrointestinal ulcers and bleeding, edema, hypertension, congestive heart failure, renal dysfunction, severe skin reactions such as Stevens-Johnson syndrome and toxic epidermal necrolysis, anaphylaxis, and most recently, an increased risk of thrombotic cardiovascular events.

SUMMARY OF THE INVENTION

Described herein are pharmaceutical compositions having a reduced dose of acetaminophen for intravenous administration, and methods of using these compositions for treating and/or preventing pain and/or fever in a subject.

In some embodiments, the pharmaceutical compositions described herein comprise less than about 1 gram of acetaminophen, wherein the pharmaceutical composition is provided as a formulation suitable for intravenous administration. For example, various embodiments may comprise about 500 mgs to about 1 gram, or about 500 mgs to about 800 mgs, or about 500 mgs to about 750 mgs. In various embodiments, the pharmaceutical compositions described herein comprise about 600 mg to about 700 mg of acetaminophen.

In some embodiments, the pharmaceutical compositions described herein further comprise at least one antioxidant. In some embodiments, the at least one antioxidant comprises cysteine hydrochloride monohydrate, thiolyglycolic acid, thiolacetic acid, dithiothreitol, reduced glutathione, thiourea, alpha-thioglycerol, cysteine, acetylcysteine, or mercaptoethane sulfonic acid, ascorbic acid ascorbic acid derivatives, an organic compound having at least one thiol, an alkyl polyhydroxylated compound, or a cycloalkyl polyhydroxylated compound.

In some embodiments, the pharmaceutical composition further comprises a buffering agent (e.g., disodium phosphate dehydrate). In some embodiments, the pharmaceutical composition has a pH from about 4 to about 8 when in solution. In some embodiments, the pharmaceutical composition has a pH of about 5 to about 6 when in solution.

In some embodiments, the pharmaceutical composition has an osmolality from about 250 mOsm/L to about 400 mOsm/L when in solution. In some embodiments, the pharmaceutical composition further comprises an isotonicity agent. In some embodiments, the isotonicity agent is dextrose, mannitol, or lactose.

In some embodiments, the pharmaceutical composition further comprises at least one analgesic agent other than acetaminophen. In some embodiments, the at least one analgesic agent other than acetaminophen comprises an anilide, an opioid, an NSAID, a cannabinoid, a pyrazolone, or a barbiturate.

In some embodiments, the pharmaceutical composition further comprises EDTA.

In a further aspect provided herein is a method for preventing or reducing pain or fever in a subject in need thereof, comprising administering to the subject, by an intravenous route of administration, a pharmaceutical compositions described herein. In some embodiments, the administration is repeated at least once with an interval of about 3 to about 5 hours. In some embodiments, the administration is repeated at least six times in a period of twenty four hours. In various embodiments, the administration is repeated three to eight times (e.g., 3 times, 4 times, five times, six times, seven times, or eight times) in a period of twenty four hours and about 3 to about 5 grams of acetaminophen (e.g., about 3 grams, about 4 grams or about 5 grams) is delivered over the twenty four hour period. In other embodiments, the administration is repeated three to eight times in a period of twenty four hours and less than about 4 grams of acetaminophen is delivered over the twenty four hour period.

In some embodiments, the pharmaceutical formulation for IV administration is a solution comprising: about 600 mg to about 700 mg of acetaminophen, cysteine hydrochloride monohydrate, disodium phosphate dehydrate, and mannitol, wherein the solution has a pH of between about 5 and about 6 and an osmolality of between about 200-400 mOsm/L. In some embodiments, the pharmaceutical composition in solution has an acetaminophen concentration of about 0.5% (w/v) to about 10% (w/v). In some embodiments, the acetaminophen concentration is about 1% (w/v). In some embodiments, the pharmaceutical composition to be administered further comprises EDTA.

In some embodiments, the subject to be treated is suffering from an infection. In some embodiments, the subject to be treated is suffering from a fever. In some embodiments, the subject to be treated is unconscious, sedated, fasting, nauseous, or unable to be administered a pharmaceutical composition by an oral route.

In some embodiments, the pharmaceutical composition is administered to the subject after a surgical intervention. In some embodiments, the pharmaceutical composition is administered within three hours of a surgical intervention on the subject. In some embodiments, the pharmaceutical composition is administered within 1 hour of a surgical intervention on the subject. In some embodiments, the pharmaceutical composition is administered postoperatively. In some embodiments, the subject to be treated is suffering from postoperative pain.

In various embodiments the pharmaceutical compositions described herein are administered as a pretreatment.

In another aspect provided herein is a method for preventing or reducing pain or fever in a subject in need thereof, comprising administering to the subject, by an intravenous route of administration, a pharmaceutical composition described herein.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

To date, the standard intravenous (IV) dose of acetaminophen for the relief of pain or fever has been 1000 mg in adults and adolescents weighing at least 50 kg. At this dose level, the frequency of acetaminophen administration is limited to a maximum of once every six hours (i.e., four administrations per twenty four hours) to minimize the potential for hepatotoxicity. On the other hand, it has generally been noted that acetaminophen has greatest efficacy during its initial rise in plasma concentration, i.e., during the first few hours post-administration, and is less effective later on after the plasma concentration of the drug drops from its peak. While not wishing to be bound by theory, it is thought that this change in efficacy is likely due to a time and concentration-dependent modulation of the central and peripheral nociceptive pathways through which acetaminophen acts.

Further, if the duration of effect of a 1000 mg dose of acetaminophen is shorter in duration than 6 hours, the use of this dose is limited since dosing more frequently than every 6 hours, e.g., every 4 hours, leaves a gap in coverage due to the 4 g acetaminophen maximum daily limit. In the treatment of fever, a dose less than 1000 mg may be fully effective due to the fact that a lower plasma level (compared to that needed for pain) is needed to effectively reduce fever.

Thus, intravenous administration of a reduced dose of acetaminophen, as described herein, permits more frequent IV acetaminophen administration to yield better overall relief of symptoms for many patients while avoiding any potential gap artificially created by the daily limit.

Also, the reduced acetaminophen IV dose affords greater flexibility to the physician in customizing treatments to the needs of the patient, selecting the dose of other drugs for use in combination therapies and allowing for smoother transitions to oral products containing acetaminophen.

Accordingly, described herein are reduced IV dose formulations of acetaminophen for intravenous administration and the use of reduced IV doses of acetaminophen for use for the treatment or prevention of pain and/or fever.

Certain Terminology

Unless defined otherwise, all technical and scientific terms used herein have the same meaning as is commonly understood by one of skill in the art to which the claimed subject matter belongs. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more.

The terms "effective amount," "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising the compound as disclosed herein required to provide a clinically significant decrease in pain. An additional example is that an "effective amount" may be a dosage that decreases a fever. An appropriate "effective" amount in any individual case may be determined using techniques, such as a dose escalation study.

The terms "administer," "administering," "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, *Pharmaceutical Sciences* (current edition), Mack Publishing Co., Easton, Pa. In preferred embodiments, the compositions comprising acetaminophen as described herein are administered intravenously.

The term "acceptable" as used herein, with respect to a formulation, composition or ingredient, means having no persistent detrimental effect on the general health of the subject being treated.

The term "antioxidant" refers to a compound that prevents oxygen or oxygen-derived free radicals from interacting with other substances. Antioxidants are added to minimize or retard oxidative processes that occur with some drugs or excipients upon exposure to oxygen or in the presence of free radicals. These processes can often be catalyzed by light, temperature, hydrogen on concentration, presence of trace metals or peroxides.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

"Concurrent administration," "administered in combination" or similar phrases referring to the acetaminophen and at least one additional component means that the components are administered concurrently to the mammal being treated. By "concurrently," it is meant that each component may be administered at the same time or sequentially in any order at different points in time. However, if not administered at the same time, they should be administered sufficiently closely in time so as to provide the desired enhancement of treatment effect. Suitable dosing intervals and the order of administration with such compounds will be readily apparent to those skilled in the art, once armed with the present disclosure. Preferably both components are administered at the same time or within the same hour.

As used herein, the term "animal" shall refer to a vertebrate animal. More preferably, the vertebrate animal is a mammal. As used herein, the term "mammal" shall refer to the Mammalia class of higher vertebrates. The term "mammal" includes, but is not limited to, a human.

As used herein, the term "pain" shall refer to all types of pain, including, but not limited to nociceptive pain, neuropathic pain, post-operative pain, lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, and genitourinary tract-related pain including cystitis. Levels of pain in a subject can be quantified using standard subjective assay scales of pain including, e.g., the Pain Intensity Visual Analogue Scale or Pain Intensity Categorical Scale. Likewise, levels of "pain relief" can also be quantified by a subjective assay, e.g., Time to Perceptible and Meaningful Pain Relief.

The terms "intravenous formulation," or "intravenous acetaminophen formulation" shall refer to a single dose formulation of acetaminophen that is provided as a lyophilized powder (or other solid form) that, once reconstituted in solution, is physiologically compatible with intravenous administration (e.g., by injection, infusion or otherwise). Alternatively, the terms refer to a formulation that is provided as a solution.

Reduced Dose Acetaminophen Formulations for Intravenous Administration (IV Formulations)

In some embodiments, the IV acetaminophen formulations described herein are in the form of a lyophilized powder to be reconstituted in solution under sterile conditions prior to administration. In other embodiments, the IV acetaminophen formulations are provided as sterile solutions ready for administration. Appropriate containers (e.g., vials, bottles, ampules, containers, etc.) for the IV formulations in either of the forms just described, as well as aseptic techniques are well known.

IV Acetaminophen Dosage

In various embodiments, the single dose IV acetaminophen formulation contains less than about 1 gram of acetaminophen. In some embodiments, the single dose IV acetaminophen contains about 500 to about 1000 mgs. In some embodiments, the single dose IV acetaminophen contains about 550 mgs to about 900 mgs. In some embodiments, the single dose IV acetaminophen formulations described herein contain about 550 mg to about 800 mg of acetaminophen, i.e., about 560 mg, 570 mg, 580 mg, 600 mg, 610 mg, 620 mg, 630 mg, 640 mg, 650 mg, 660 mg, 670 mg, 675 mg, 680 mg, 690 mg, 700 mg, 720 mg, 750 mg, 775 mg, or any other amount of acetaminophen from about 550 mg to about 800 mg of acetaminophen. In some embodiments, an IV acetaminophen formulation contains about 600 mg to about 700 mg of acetaminophen, i.e., about 610 mg, 620 mg, 630 mg, 640 mg, 650 mg, 660 mg, 670 mg, 680 mg, 690 mg, or any other amount of acetaminophen from about 600 mg to about 700 mg of acetaminophen. In one embodiment, the acetaminophen formulation contains about 650 mg of acetaminophen.

In some embodiments, the concentration of acetaminophen in an IV formulation solution described herein is about 0.3% (w/v) to about 12% (w/v), i.e., about 0.4%, 0.5%, 0.6%, 0.7%, 0.8%, 0.9%, 1.0%, 1.1%, 1.2%, 1.5%, 2.5%, 3%, 3.7%, 4%, 4.5%, 5%, 6%, 7%, 8%, 8.5%, 9%, 10%, 10.5%, 11%, or any other concentration from about 0.3% (w/v) to about 12% (w/v). In some embodiments the concentration of acetaminophen is about 0.7% (w/v) to about 1.4% (w/v), i.e., about 0.8%, 0.9%, 1.0%, 1.1%, 1.2%, 1.3% or any other concentration of acetaminophen from about 0.7% (w/v) to about 1.4% (w/v). In one embodiment, the concentration of acetaminophen is about 1.0% (w/v).

In some embodiments, the volume of an IV acetaminophen formulation solution is about 30 to about 200 ml, i.e., about 30, 35, 40, 45, 55, 60, 65, 75, 80, 85, 90, 92, 95, 100, 105, 110, 125, 130, 150, 175, 180, or another volume of IV formulation solution from about 30 to about 200 ml. In some embodiments, the volume of the IV formulation is about 75 to about 125 ml. In another embodiment the volume is about 40 to about 75 ml. In one embodiment, the volume of the IV formulation is about 100 ml.

Antioxidants

Generally, the acetaminophen formulations described herein also contains at least one antioxidant to increase the stability of acetaminophen in solution. Examples of suitable antioxidants include, but are not limited to, cysteine hydrochloride monohydrate, thiolyglycolic acid, thiolacetic acid, dithiothreitol, reduced glutathione, thiourea, alpha-thioglycerol, cysteine, acetylcysteine, methionine, mercaptoethane sulfonic acid, metabisulfite, ascorbic acid ascorbic acid derivatives (e.g., ascorbyl palmitate), sodium citrate, an organic compound having at least one thiol, an alkyl polyhydroxylated compound, a cycloalkyl polyhydroxylated compound, a hydroxypolycarboxylic acid, an alpha-hydroxypolycarboxylic acid (e.g., citric acid), tocotrienol, dimethyl glycine, betaine, butylated hydroxyanisole, butylated hydroxytoluene, tocopherol, tocopherol polyethylene glycol succinate, butylated hydroxytoluene (BHT), butylated hydroxyanisole (BHA), propyl gallate, hydroquinone, hydroxycoumarins, ethanolamine, lecithin, cephalin, malic acid, sorbitol, phosphoric acid, thiodipropionic acid and its esters, dithiocarbamates or any combination thereof. In one embodiment, the acetaminophen formulation is free of polyethylene glycol or a derivative thereof. In another embodiment, the acetaminophen formulation is free of sulfites. In one embodiment, the antioxidant is cysteine hydrochloride monohydrate. In yet another embodiment, the antioxidant is mannitol.

In some embodiments, the amount % (w/w) of the antioxidant in the solid form of the IV formulation (i.e., prior to preparation in solution) is about 0.10% (w/w) to about 5.0% (w/w), i.e., 0.15% (w/w), 0.17% (w/w), 0.20% (w/w), 0.30% (w/w), 0.40% (w/w), 0.45% (w/w), 0.50% (w/w), 0.52% (w/w), 0.55% (w/w), 0.60% (w/w), 0.70% (w/w), 0.80% (w/w), 1.0% (w/w), 1.3% (w/w), 1.5% (w/w), 1.7% (w/w), 2.0% (w/w), 2.2% (w/w), 2.3% (w/w), 2.5% (w/w), 2.7%, 2.8%, 3.0% (w/w), 3.2%, 3.5% (w/w), 3.6% (w/w), 4.0% (w/w), 4.7% (w/w), or any other amount of antioxidant % (w/w) from about 0.10% (w/w) to about 5.0% (w/w). In some embodiments, the amount % (w/w) of antioxidant is about 0.30% (w/w) to about 1.0% (w/w). In one embodiment, the amount % (w/w) of antioxidant is about 0.50% (w/w).

In some embodiments, the concentration of the antioxidant in an IV formulation solution prior to administration ranges from about 0.01 mg/ml to about 10 mg/ml, i.e., 0.02 mg/ml, 0.03 mg/ml, 0.05 mg/ml, 0.08 mg/ml, 0.09 mg/ml, 0.10 mg/ml, 0.12 mg/ml, 0.13 mg/ml, 0.15 mg/ml, 0.18 mg/ml, 0.20 mg/ml, 0.22 mg/ml, 0.25 mg/ml, 0.27 mg/ml, 0.30 mg/ml, 0.40 mg/ml, 0.45 mg/ml, 0.50 mg/ml, 0.60 mg/ml, 0.80 mg/ml, 1.2 mg/ml, 1.5 mg/ml, 2.0 mg/ml, 2.5 mg/ml, 3.0 mg/ml, 3.5 mg/ml, 4.0 mg/ml, 5.0 mg/ml, 6.0, mg/ml 7.5 mg/ml, 8.0 mg/ml, 9 mg/ml, 9.5 mg/ml, or any other concentration of antioxidant from about 0.01 mg/ml to about 10 mg/ml. In some embodiments, the concentration of antioxidant is about 0.08 mg/ml to about 0.50 mg/ml. In one embodiment, the concentration of antioxidant is about 0.25 mg/ml.

Buffering Agents

In some embodiments, an IV acetaminophen formulation contains at least one buffering agent to maintain the pH of the formulation within an acceptable range as described herein. The buffer used is a buffer compatible with parenteral administration in humans, the pH of which may be adjusted between 4 and 8. In some embodiments, the pH of an IV acetaminophen formulation is from about pH 4 to about pH 8, i.e., pH 4.5, pH 4.6, pH 4.8, pH 5.0, pH 5.5, pH 6.2, pH 6.5, pH 7.5, or any other pH value from about pH 4 to about pH 8. In some embodiments, the pH of the IV acetaminophen formulation is from about pH 5 to about pH 7.0, i.e., about pH 5.2, pH 5.5, pH 5.6, pH 6.0, pH, 6.4, or any other pH value from about pH 5 to about pH 7.0. In one embodiment, the IV acetaminophen formulation has a pH of about 5 to about 6.

In some embodiments, buffering agents have a pKa from about 4.5 to about 6.5, i.e., 4.6, 4.8, 5.0, 5.2, 5.3, 5.4, 5.5, 5.8, 6.0, 6.2, 6.4, or any other pKa from about 4.5 to about 6.5.

In some embodiments, the buffering agent is a pharmaceutically acceptable salt or acid of citrate, phosphate, acetate, glutamate, tartrate, benzoate, lactate, histidine or other amino acids, gluconate, malate, succinate, formate, propionate, carbonate, or any combination thereof adjusted to an appropriate pH, as described herein, with acid (e.g., hydrochloric acid) or base (e.g., sodium hydroxide) as required. In one embodiment, the buffering agent is disodium phosphate dehydrate.

In some embodiments, the amount % (w/w) of the buffering agent in the solid form of the IV formulation (i.e., prior to preparation in solution) is about 0.05% (w/w) to about 2% (w/w), i.e., about 0.08% (w/w), 0.10% (w/w), 0.15% (w/w), 1.0% (w/w), 1.3% (w/w), 1.5% (w/w), 1.7% (w/w), 0.20% (w/w), 0.22% (w/w), 0.25% (w/w), 0.26% (w/w), 0.27% (w/w), 0.28% (w/w), 0.30% (w/w), 0.35% (w/w), 0.40% (w/w), 0.50% (w/w), 0.60% (w/w), 0.70% (w/w), 0.80% (w/w), 1.2% (w/w), 1.4% (w/w), 1.5% (w/w), 1.7%, or any other amount of buffering agent % (w/w) from about 0.05% (w/w) to about 2.0% (w/w). In some embodiments, the amount % (w/w) of the buffering agent is about 0.10% to about 0.70%. In one embodiment, the amount % (w/w) of the buffering agent is about 0.26%.

In some embodiments, the concentration of the buffering agent in an IV formulation solution prior to administration ranges from about 0.01 mg/ml to about 10 mg/ml, i.e., 0.02 mg/ml, 0.03 mg/ml, 0.05 mg/ml, 0.08 mg/ml, 0.09 mg/ml, 0.10 mg/ml, 0.12 mg/ml, 0.13 mg/ml, 0.15 mg/ml, 0.30 mg/ml, 0.5 mg/ml, 0.8 mg/ml, 1.2 mg/ml, 1.5 mg/ml, 2.0 mg/ml, 2.5 mg/ml, 3.0 mg/ml, 3.5 mg/ml, 4.0 mg/ml, 5.0 mg/ml, 6.0, mg/ml 7.5 mg/ml, 8.0 mg/ml, 9 mg/ml, 9.5 mg/ml, or any other concentration of buffering agent from about 0.01 mg/ml to about 10 mg/ml. In some embodiments, the concentration of buffering agent is about 0.08 mg/ml to about 0.30 mg/ml. In one embodiment, the concentration of buffering agent is about 0.13 mg/ml.

Isotonicity Agents

In some embodiments, an IV acetaminophen formulation also contains one or more isotonicity agents to maintain the osmolality of the formulation in a range that is physiologically compatible with IV administration. In some embodiments, the osmolality of the IV acetaminophen formulation is about 230 mOsm/L to about 420 mOsm/L, i.e., about 240 mOsm/L, 250 mOsm/L, 260 mOsm/L, 270 mOsm/L, 280 mOsm/L, 290 mOsm/L, 300 mOsm/L, 305 mOsm/L, 310 mOsm/L, 320 mOsm/L, 350 mOsm/L, 375 mOsm/L, 400 mOsm/L or any other osmolality from about 240 mOsm/L to about 420 mOsm/L. In some embodiments, the osmolality of the IV acetaminophen formulation is about 280 mOsm/L to about 320 mOsm/L, i.e., about 290 mOsm/L, 295 mOsm/L, 300 mOsm/L, 305 mOsm/L, 310 mOsm/L, 315 mOsm/L, or any other osmolality from about 280 mOsm/L to about 320 mOsm/L. In one embodiment, the osmolality of the IV acetaminophen formulation is about 200-400 mOsm/L.

Suitable agents for adjusting the isotonicity of IV acetaminophen formulations include, but are not limited to, mannitol, sorbitol, glycerol, sucrose, glucose, dextrose, levulose, fructose, lactose, polyethylene glycols 400 to 4000, phosphates, sodium chloride, potassium chloride, calcium chloride, calcium gluconoglucoheptonate, dimethyl sulfone. In one embodiment, the isotonicity agent is mannitol.

In some embodiments, the amount % (w/w) of the isotonicity agent in the solid form of the IV formulation (i.e., prior to preparation in solution) is about 5% (w/w) to about 95% (w/w), i.e., about 10% (w/w), 15% (w/w), 20% (w/w), 25% (w/w), 30% (w/w), 35% (w/w), 40% (w/w), 45% (w/w), 50% (w/w), 55% (w/w), 60% (w/w), 65% (w/w), 70% (w/w), 72% (w/w), 74% (w/w), 76% (w/w), 78% (w/w), 79% (w/w), 80%

(w/w), 81% (w/w), 82% (w/w), 84% (w/w), 86% (w/w), 90% (w/w), 92% (w/w), or any other amount of isotonicity agent % (w/w) from about 5% (w/w) to about 95% (w/w). In some embodiments, the amount of isotonicity agent % (w/w) is about 65% (w/w) to about 85% (w/w). In one embodiment, the amount of isotonicity agent % (w/w) is about 79%.

In some embodiments, the concentration of the isotonicity agent in an IV formulation solution prior to administration ranges from about 1.0 mg/ml to about 150 mg/ml, i.e., 1.0 mg/ml, 2.0 mg/ml, 3.0 mg/ml, 3.5 mg/ml, 4.0 mg/ml, 4.5 mg/ml, 5.0 mg/ml, 8.0 mg/ml, 12 mg/ml, 15 mg/ml, 20 mg/ml, 25 mg/ml, 30 mg/ml, 32 mg/ml, 35 mg/ml, 37 mg/ml, 38 mg/ml, 40 mg/ml, 50 mg/ml, 60, mg/ml, 75 mg/ml, 80 mg/ml, 90 mg/ml, 95 mg/ml, 100, 110, 120, 140, or any other concentration of buffering agent from about 5 mg/ml to about 150 mg/ml. In some embodiments, the concentration of buffering agent is about 0.08 mg/ml to about 0.30 mg/ml. In one embodiment, the concentration of buffering agent is about 0.13 mg/ml.

Stabilizers

In some embodiments, IV acetaminophen formulations described herein also include a stabilizer, e.g., a chelating agent such as ethylene diamino tetraacetic acid (EDTA), ethylene diamino, N,N'-diacetic-N,N'-dipropionic acid, ethylene diamino tetraphosphonic acid, 2,2'-(ethylene diamino) dibutyric acid, nitrilotriacetic, acid, or ethylene-glycol bis (diaminoethyl ether) N,N,N',N'-tetraacetic acid and sodium or calcium salts thereof. In some embodiments, the IV acetaminophen formulation includes EDTA as the stabilizer.

In some embodiments, the IV acetaminophen formulations described herein contain a stabilizer in the amount of about 0.005 to about 1.0 mg/ml. In some embodiments, the stabilizer is present in an amount of about 0.01 mg/ml, 0.05 mg/ml, 0.1 mg·ml, 0.5 mg/ml, or 1.0 mg/ml.

In some embodiments, to reduce oxidation of acetaminophen in solution and thereby increase its stability, oxygen is removed from an IV formulation solution by bubbling an inert gas (e.g., argon or nitrogen) through the solution under sterile conditions. Methods for minimizing oxidative degradation of acetaminophen solutions during storage are described in further detail in, e.g., U.S. Pat. No. 6,992,218, which is incorporated herein by reference in its entirety.

Methods of Treatment

In many cases, IV administration of acetaminophen is considered the most suitable route of administration for expedient and efficacious relief of a patient's pain or fever, particularly in a hospital setting. In some embodiments, a subject to be administered an IV formulation of acetaminophen (e.g., an adult subject or adolescent weighing at least about 50 kg), as described herein, is unconscious, sedated, fasting, nauseous, or unable to be administered a pharmaceutical composition by an oral route. Additionally, the rectal route is associated with highly variable bioavailability and slow absorption, and in children, the efficacious rectal dose exposes some pediatric patients to a potentially toxic exposure. In some embodiments, a patient suffering from pain or fever is in need of a faster onset of pain relief or fever treatment than possible by acetaminophen administration through an administration route other than by an IV administration.

In some embodiments, the IV formulations described herein are used as a pretreatment to another therapy. In some of these embodiments, pretreatment with an IV formulation described herein allows the use of a lower dose of acetaminophen. In some embodiments, the IV formulation described herein is administered before chemotherapy treatment, radiation treatment, a biopsy, or a blood transfusion. It should be understood that these are non-limiting examples and that the IV formulations described herein can be administered as a pretreatment to any therapy where pain and/or fever are predicted to occur.

The IV formulations described herein can be used for reducing pain conditions including, but not limited to, acute nociceptive pain, acute neuropathic pain, postoperative pain, lower back pain, cluster headaches, herpes neuralgia, phantom limb pain, central pain, dental pain, opioid-resistant pain, visceral pain, surgical pain, procedural pain, bone injury pain, pain during labor and delivery, pain resulting from burns, post partum pain, headache, muscular aches, backache, arthritis pain, the common cold, toothache, dental pain, osteoarthritis pain, menstrual pain, menstrual cramps, migraine, and genitourinary tract-related pain including cystitis. In some embodiments, the IV formulation is administered preemptively to a subject, i.e., prior to the onset of pain or a pain-inducing condition or stimulus (e.g., a surgical operation). In some embodiments, the IV formulations described herein are used to reduce fever, including, but not limited to, fever due to infections, drug reactions, allergic reactions, transfusion reactions, stroke, surgery, heat stroke, rheumatic diseases, cancer, or fever of unknown origin. In some embodiments, the IV formulations described herein are administered to a patient undergoing a dental procedure.

In some embodiments, the IV formulation is administered to a subject after undergoing a surgical intervention, e.g., within about 12 hours after a surgical intervention, i.e., within 11 hours, 10 hours, 9 hours, 8 hours, 6 hours, 5 hours, 4 hours, 3 hours, 2 hours, 1 hours, 45 minutes, 30 minutes 15 minutes, 5 minutes, or any period within about 12 hours following a surgical intervention.

In some embodiments, a subject is administered the IV formulation prior to a surgical intervention, e.g., about 4 hours or less prior to the surgical intervention, i.e., about 3 hours, 2 hours, 1 hours, 30 minutes, 15 minutes or even during the surgical intervention itself.

Depending on the concentration of acetaminophen in an IV formulation solution and consistent with the acetaminophen dose levels described herein, the volume of IV formulation solution to be administered can vary from about 1 mL to about 200 mL, e.g., 5 mL, 10 mL, 20 mL, 25 mL, 30 mL, 40 mL, 50 mL, 60 mL, 65 mL, 70 mL, 85 mL, 90 mL, 100 mL, 110 mL, 120 mL, 130 mL, 140 mL, 150 mL, 160 mL, 180 mL, or any other volume of IV formulation solution from about 1 mL to about 200 mL.

In some embodiments, the amount of time required for administration of the IV formulation ranges from about 1 minute to about 1 hours, i.e., about 5 minutes, 10 minutes, 11 minutes, 15 minutes, 20 minutes, 30 minutes, 45 minutes, or any other administration time from about 1 minute to about 1 hour. In some embodiments, the amount of time required for administration of the IV formulation ranges from about 5 minutes to about 45 minutes, or about 5 minutes to about 30 minutes, or about 5 minutes to about 15 minutes.

Depending on the severity and persistence of a subject's condition, and in accordance with a medical caregiver's judgment, an IV formulation dose of acetaminophen, as described herein, can be administered in an interval to allow for the administration of about 3 to about 5 grams in a 24 hour period. In some embodiments, the IV formulation of acetaminophen is administered in an interval sufficient to allow for the administration of about 4 grams in a 24 hour period. In some embodiments, the IV formulation is administered between 1 to 6 times, i.e., 1, 2, 3, 4, 5, 6 times every twenty four hours, as deemed necessary by a medical caregiver. In some embodiments, the frequency of administration is not greater than once every four hours.

In various embodiments, the IV formulation of acetaminophen is dosed so as to provide less than about 4 grams over a 24 hour period. In various embodiments, the IV formulation of acetaminophen is dosed three to six times in a 24 hour period. For example, in some embodiments, the IV formulation of acetaminophen is dosed three times in a 24 hour period. In other embodiments, the IV formulation of acetaminophen is dosed four times in a 24 hour period. In still other embodiments, the IV formulation of acetaminophen is dosed five times in a 24 hour period. In some embodiments, the IV formulation of acetaminophen is dosed six times in a 24 hour period. In some embodiments, the IV formulation of acetaminophen is dosed seven times in a 24 hour period. In some embodiments, the IV formulation of acetaminophen is dosed eight times in a 24 hour period.

Combination Therapies

The acetaminophen IV formulations described herein can also be used in combination with other therapeutic reagents, e.g., other analgesics, antipyretics, or anti-inflammatory agents that are selected for their therapeutic or palliative value. In general, where a combination therapy is employed, other agents do not have to be administered in the same pharmaceutical composition as acetaminophen, and may, because of different physical and chemical characteristics, be administered by different routes. The determination of the mode of administration and the advisability of administration, where possible, in the same pharmaceutical composition, is well within the knowledge of the skilled clinician with the teachings described herein. The initial administration of either the IV acetaminophen formulation or the one or more therapeutic agents (e.g., analgesic agents other than acetaminophen) to be used in combination with acetaminophen can be made according to established protocols known in the art, and then, based upon the observed effects, the dosage, modes of administration and times of administration can be modified by the skilled clinician.

The particular choice of compounds (e.g., analgesic agents) for use in combination with the IV acetaminophen formulation described herein will depend on the diagnosis of the attending physicians (or other medical caregivers) and their judgment of the condition of the patient and the appropriate treatment protocol. The compounds may be administered concurrently (e.g., simultaneously, essentially simultaneously or within the same treatment protocol) or sequentially, depending upon the severity of pain experienced by the patient, the nature of the disease, disorder, or condition, the condition, and the actual choice of compounds used. The determination of the order of administration, and the number of repetitions of administration of each therapeutic agent during a treatment protocol, is well within the knowledge of the skilled physician after evaluation of the disease being treated and the condition of the patient.

For combination therapies described herein, dosages of the compounds to be co-administered with an acetaminophen IV formulation will vary depending on the type of co-drug employed, on the amount of pain experienced by the patient, the risk for addiction, the disease or condition being treated and so forth. In addition, when co-administered with one or more biologically active agents, the acetaminophen IV formulation provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is an acetaminophen IV formulation described herein) may be administered in any order or even simultaneously. If simultaneously, the multiple therapeutic agents may be provided in a single, unified IV form, or in multiple forms (by way of example only, either as a single IV formulation, as multiple IV formulations, or as IV formulation and a pill). One of the therapeutic agents may be given in multiple doses, or both may be given as multiple doses. If not simultaneous, the timing between the multiple doses may vary from more than 1 minute to less than 12 hours. In some embodiments, the timing between the multiple doses is from between about 1 minute to about 6 hours, or about 1 minute and about 3 hours, or about 1 minute and about 1 hour. In addition, the combination methods, compositions and formulations are not to be limited to the use of only two agents; the use of multiple therapeutic combinations is also envisioned.

The pharmaceutical agents which make up the combination therapy disclosed herein may be a combined dosage form (i.e., a combined IV formulation) or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent.

The compounds described herein and combination therapies can be administered before, during or after the occurrence of a fever or painful condition, and the timing of administering the composition containing a compound can vary. Thus, for example, the compounds can be used as a prophylactic and can be administered continuously to subjects with a propensity to develop conditions (e.g., body aches and chills following chemotherapy treatment) or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms.

A compound is preferably administered as soon as is practicable before or after the onset of a painful condition (e.g., postoperative pain), and for a length of time necessary for the treatment of the disease, such as, for example, from about 1 month to about 3 months.

Exemplary Analgesic Agents for Use in Combination with an Acetaminophen IV Formulation Opioids In some embodiments, an acetaminophen IV formulation described herein is used in any combination with one or more opioids, which include, but are not limited to allylprodine, alphamethylfentanyl, alfentanil, bezitramide, buprenorphine, butorphanol, carfentanyl, codeine, dextropropoxyphene, dextromoramide, dezocine, diacetylmorphine, dihydrocodeine, dipapanone, dismorphine, dihydrocodeine, etorphine, fentanyl, hydrocodone, hydromorphone, ketobemidone, lefetamine, levorphanol, levo-alphacetylmethadol, levomethorphan, meptazinol, methadone, morphine, nalbuphine, nicomorphine, ohmefentanyl, opium, oripavine, oxycodone, oxymorphone, methadone, PEPAP, pentazocine, pethidine, phenazocine, piritamide, prodine, propoxyphene napsylate, remifentanil, sufentanil, tilidine, thebaine, tramadol, and tapentadol.

Non-Steroidal Anti-Inflammatory Drugs (NSAIDs)

In some embodiments, an acetaminophen IV formulation described herein is used in any combination with one or more NSAIDs, which include, but are not limited to amoxiprin, benorilate, choline magnesium salicylate, diflusinal, faislamine, methyl salicylate, magnesium salicylate, salicyl salicylate, diclofenac, aceclofenac, acemetacin, bromfenac, ethenzamide, etodolac, indometacin, nabumetone, sulindac, tolmetin, carprofen, fenbufen, fenoprofen, flurbiprofen, ketoprofen, ketorolac, loxoprofen, naproxen, oxaprozin, tiaprofenic acid, suprofen, mefenamic acid, meclofenamic acid, phenylbutazone, metamizole, oxyphenbutazone, sulfinpyrazone, piroxicam, lornoxicam, meloxicam, tenoxicam, nimesulide salixylates, arylalkanoic acids, 2-arylpropionic acids (profens), n-arylanthranilic acids (fenamic acids), pyrazolidine derivatives, oxicams, and COX-2 inhibitors.

Other Analgesic Agents

In some embodiments, an acetaminophen iv formulation described herein is used in any combination with one or more analgesic agents not described above, including, but not limited to, barbiturates (e.g., butalbital), pyrazolones (e.g., aminophenazone, metamizole, phenazone), cannabinoids (e.g., tetrahydrocannabinol), ziconotide, choline magnesium fentanyl, oxycodone, codeine, dihydrocodeine, dihydrocodeinone enol acetate, morphine, desomorphine, apomorphine, diamorphine, pethidine, methadone, dextropropoxyphene, pentazocine, dextromoramide, oxymorphone, hydromorphone, dihydromorphine, noscapine, papverine, papveretum, alfentanil, buprenorphine, tramadol and pharmaceutically acceptable salts, derivatives, homologs or analogs thereof as well as opioid agonists.

Exemplary Antiemetic Agents for Use in Combination with an Acetaminophen IV Formulation In some embodiments, an acetaminophen iv formulation described herein is used in any combination with one or more antiemetic agents not described above, including, but not limited to, antihistamines (e.g., Cyclizine, Diphenhydramine, Dimenhydrinate, Meclizine, Promethazine, Pentazine, Phenergan, Promacot, or Hydroxyzine); 5-HT$_3$ receptor antagonists (e.g., Dolasetron, Granisetron, Ondansetron, Tropisetron, or Palonosetron); and dopamine antagonists (e.g., Domperidone, Droperidol, haloperidol, chlorpromazine, promethazine, prochlorperazine, or metoclopramide).

Kits

In some embodiments provided herein are kits that can simplify the administration of an IV acetaminophen formulation to a patient. In some embodiments, a kit comprises a unit dosage form of an acetaminophen IV formulation as described herein provided as a sterile lyophilate to be reconstituted by addition of sterile water. In other embodiments, the IV formulation is provided as a sterile degassed solution ready for administration. The kit can further comprise a label or printed instructions on the use of the acetaminophen IV formulation to treat pain or fever. The kit can also further comprise a unit dosage form of another therapeutic agent, for example, a container containing an effective amount of a second analgesic agent for use in combination with the acetaminophen IV formulation. In some embodiments, a kit further comprises a device that is useful for administering the IV formulation unit dosage forms. Examples of such a device include, but are not limited to, a syringe or a drip bag.

While preferred embodiments of the present invention have been shown and described herein, it will be understood that such embodiments are provided by way of example only. Numerous variations, changes, and substitutions can be made without departing from the scope of the invention. It should be understood that various alternatives to the embodiments of the invention described herein may be employed in practicing the invention. It is intended that the following claims define the scope of the invention and that methods and structures within the scope of these claims and their equivalents be covered thereby. Thus, these examples should not be read as limiting the example in any way. For example, different amounts of the components described in the following examples as well as the components themselves can be changed according to the disclosure provided herein.

EXAMPLES

Example 1

IV Acetaminophen Formulations

TABLE 1

| Exemplary IV Formulation of Acetaminophen | |
|---|---|
| Acetaminophen | 0.550 g-1.000 g |
| Excipients: | |
| Antioxidant | 0.0100-0.0200 g |
| pH modulator(s) | qs pH 5-6 |
| Buffer | 0.005-0.01 g |
| Isotonic Agent | 1.5-3.5 g |
| Solvent | qs 50.0-100.0 mL |

Example 1A

IV Acetaminophen Formulations

Example 1A is prepared according to the procedure outlined in Example 2 using the amounts of the excipients described in Example 1.

| | Formula 1(A) | | | | |
|---|---|---|---|---|---|
| | Acetaminophen | | | | |
| Excipients: | 0.550 g | 0.650 g | 0.750 g | 0.850 g | 0.950 g |
| Antioxidant | Reduced Glutathione | Reduced Glutathione | Reduced Glutathione | Reduced Glutathione | Reduced Glutathione |
| pH Modulator | Sodium hydroxide | Sodium hydroxide | Sodium hydroxide | Sodium hydroxide | Sodium hydroxide |
| pH Modulator | Hydrochloric Acid | Hydrochloric Acid | Hydrochloric Acid | Hydrochloric Acid | Hydrochloric Acid |
| Buffering Agent | Sodium Citrate | Sodium Citrate | Sodium Citrate | Sodium Citrate | Sodium Citrate |

-continued

| | Formula 1(A) | | | | |
|---|---|---|---|---|---|
| | Acetaminophen | | | | |
| Excipients: | 0.550 g | 0.650 g | 0.750 g | 0.850 g | 0.950 g |
| Isotonicity Agent | Sodium Chloride | Sodium Chloride | Sodium Chloride | Sodium Chloride | Sodium Chloride |
| Solvent | Sterile Water for injection | Sterile Water for injection | Sterile Water for injection | Sterile Water for injection | Sterile Water for injection |

Example 1B

IV Acetaminophen Formulations

Example 1B is prepared according to the procedure outlined in Example 2 using the amounts of the excipients described in Example 1.

| | Formula 1(B) | | | | |
|---|---|---|---|---|---|
| | Acetaminophen | | | | |
| Excipients: | 0.550 g | 0.650 g | 0.750 g | 0.850 g | 0.950 g |
| Antioxidant | Methionine | Methionine | Methionine | Methionine | Methionine |
| pH Modulator | Sodium hydroxide | Sodium hydroxide | Sodium hydroxide | Sodium hydroxide | Sodium hydroxide |
| pH Modulator | Hydrochloric Acid | Hydrochloric Acid | Hydrochloric Acid | Hydrochloric Acid | Hydrochloric Acid |
| Buffering Agent | Sodium Acetate | Sodium Acetate | Sodium Acetate | Sodium Acetate | Sodium Acetate |
| Isotonicity Agent | Mannitol | Mannitol | Mannitol | Mannitol | Mannitol |
| Solvent | Sterile Water for injection | Sterile Water for injection | Sterile Water for injection | Sterile Water for injection | Sterile Water for injection |

Example 1C

IV Acetaminophen Formulations

Example 1C is prepared according to the procedure outlined in Example 2 using the amounts of the excipients described in Example 1.

| | Formula 1(C) | | | | |
|---|---|---|---|---|---|
| | Acetaminophen | | | | |
| Excipients: | 0.550 g | 0.650 g | 0.750 g | 0.850 g | 0.950 g |
| Antioxidant | Cysteine Hydrocloride Monohydrate | Cysteine Hydrocloride Monohydrate | Cysteine Hydrocloride Monohydrate | Cysteine Hydrocloride Monohydrate | Cysteine Hydrocloride Monohydrate |
| pH Modulator | Sodium hydroxide | Sodium hydroxide | Sodium hydroxide | Sodium hydroxide | Sodium hydroxide |
| pH Modulator | Hydrochloric Acid | Hydrochloric Acid | Hydrochloric Acid | Hydrochloric Acid | Hydrochloric Acid |
| Buffering Agent | Disodium Phosphate Dehydrate | Disodium Phosphate Dehydrate | Disodium Phosphate Dehydrate | Disodium Phosphate Dehydrate | Disodium Phosphate Dehydrate |
| Isotonicity Agent | Mannitol | Mannitol | Mannitol | Mannitol | Mannitol |
| Solvent | Sterile Water for injection | Sterile Water for injection | Sterile Water for injection | Sterile Water for injection | Sterile Water for injection |

Example 1D

IV Acetaminophen Formulations

Example 1D is prepared according to the procedure outlined in Example 2 using the amounts of the excipients described in Example 1.

| | Formula 1(D) | | | | |
|---|---|---|---|---|---|
| | Acetaminophen | | | | |
| Excipients: | 0.550 g | 0.650 g | 0.750 g | 0.850 g | 0.950 g |
| Antioxidant | Ascorbic Acid | Ascorbic Acid | Ascorbic Acid | Ascorbic Acid | Ascorbic Acid |
| pH Modulator | Sodium hydroxide | Sodium hydroxide | Sodium hydroxide | Sodium hydroxide | Sodium hydroxide |
| pH Modulator | Hydrochloric Acid | Hydrochloric Acid | Hydrochloric Acid | Hydrochloric Acid | Hydrochloric Acid |
| Buffering Agent | Sodium Tartate | Sodium Tartate | Sodium Tartate | Sodium Tartate | Sodium Tartate |
| Isotonicity Agent | Glycerol | Glycerol | Glycerol | Glycerol | Glycerol |
| Solvent | Sterile Water for injection | Sterile Water for injection | Sterile Water for injection | Sterile Water for injection | Sterile Water for injection |

Example 1E

IV Acetaminophen Formulations

Example 1E is prepared according to the procedure outlined in Example 2 using the amounts of the excipients described in Example 1.

| | Formula 1(E) | | | | |
|---|---|---|---|---|---|
| | Acetaminophen | | | | |
| Excipients: | 0.550 g | 0.650 g | 0.750 g | 0.850 g | 0.950 g |
| Antioxidant | Acetylcysteine | Acetylcysteine | Acetylcysteine | Acetylcysteine | Acetylcysteine |
| pH Modulator | Sodium hydroxide | Sodium hydroxide | Sodium hydroxide | Sodium hydroxide | Sodium hydroxide |
| pH Modulator | Hydrochloric Acid | Hydrochloric Acid | Hydrochloric Acid | Hydrochloric Acid | Hydrochloric Acid |
| Buffering Agent | Disodium Phosphate Dehydrate | Disodium Phosphate Dehydrate | Disodium Phosphate Dehydrate | Disodium Phosphate Dehydrate | Disodium Phosphate Dehydrate |
| Isotonicity Agent | Sorbitol | Sorbitol | Sorbitol | Sorbitol | Sorbitol |
| Solvent | Sterile Water for injection | Sterile Water for injection | Sterile Water for injection | Sterile Water for injection | Sterile Water for injection |

Example 1F

IV Acetaminophen Formulations

Example 1F is prepared according to the procedure outlined in Example 2 using the amounts of the excipients described in Example 1.

| | Formula 1(F) | | | | |
|---|---|---|---|---|---|
| | Acetaminophen | | | | |
| Excipients: | 0.550 g | 0.650 g | 0.750 g | 0.850 g | 0.950 g |
| Antioxidant | metabisulfite | metabisulfite | metabisulfite | metabisulfite | metabisulfite |
| pH Modulator | Sodium hydroxide | Sodium hydroxide | Sodium hydroxide | Sodium hydroxide | Sodium hydroxide |
| pH Modulator | Hydrochloric Acid | Hydrochloric Acid | Hydrochloric Acid | Hydrochloric Acid | Hydrochloric Acid |

-continued

| | Formula 1(F) | | | | |
|---|---|---|---|---|---|
| | Acetaminophen | | | | |
| Excipients: | 0.550 g | 0.650 g | 0.750 g | 0.850 g | 0.950 g |
| Buffering Agent | Disodium Phosphate Dehydrate | Disodium Phosphate Dehydrate | Disodium Phosphate Dehydrate | Disodium Phosphate Dehydrate | Disodium Phosphate Dehydrate |
| Isotonicity Agent | Glucose | Glucose | Glucose | Glucose | Glucose |
| Solvent | Sterile Water for injection | Sterile Water for injection | Sterile Water for injection | Sterile Water for injection | Sterile Water for injection |

Example 2

Preparation of IV Formulation Solutions

Prior to storage the formulations set forth in Example 1 are subjected to bubbling with nitrogen, transferred to Type II colorless bottles, and then placed under vacuum (low pressure approx. 550 mm of Hg) before stoppering the bottles with a synthetic elastomer grey stopper crimped with an aluminum cap. The residual oxygen content is approximately 1.5 ppm of dissolved oxygen. The bottles are then sterilized at 121° C. for 15 minutes. Sterile solutions are stored at ambient temperature (less than 30° C.) for up to two years prior to use.

Example 3

A Phase III Randomized, Double-Blind, Placebo-Controlled, Multi-Center, Parallel-Group, Repeated-Dose Study of the Analgesic Efficacy and Safety of 650 mg IV Acetaminophen Versus Placebo for the Treatment of Postoperative Pain After Abdominal Laparoscopic Surgery In an effort to provide an intravenous, non-NSAID, non-opioid treatment for pain relief, the safety and efficacy of a 650 mg IV dose of APAP for the treatment of acute pain is examined.

Study Design and Evaluation

A Phase III, randomized, double-blind, Placebo-controlled, multi-center, parallel-group, repeated dose study is conducted in approximately 240 Subjects who have undergone planned or elective abdominal laparoscopic surgery. Approximately 15 to 20 US sites will participate in the Study.

Subjects will be centrally randomized, across all study centers, to receive infusions of Study Medication (either APAP or Placebo) at a dose at a dose (650 mg, 1000 mg, or placebo) and schedule described below.

Timed PI and pain relief (PR) Assessments will begin at baseline just prior to T0, the start of the first infusion of Study Medication, and continue through T24 hours.

All Subjects have access to rescue medication at all times throughout the study, as described below.

The Study will include the following assessment periods and procedures:

Screening (Day −21 to Randomization)

Screening is the period that begins when the Subject signs the Informed Consent Form and ends with randomization to Study Medication on POD1. During this period, the eligibility and baseline status of the Subject are determined.

Treatment Period (Dose 1/T0/POD1 to T24/POD2)

Administration of Study Medication (and Study-related assessments) will occur from T0 (morning of POD1) to T24 hours (morning of POD2).

Criteria for Evaluation

The primary efficacy endpoint is SPID24 (defined as the Sum of VAS score differences from baseline at T0 to T24), excluding all data after rescue medication.

Subject Selection Criteria

To be eligible for entry into the Study, Subjects must meet all of the following criteria prior to surgery: (1) Provide written Informed Consent prior to participation in the Study; (2) is scheduled to undergo abdominal laparoscopic surgery (laparoscopic gastric bypass procedures are not eligible); (3) If Subject is a female of childbearing potential, have a negative pregnancy test within 21 days of surgery; (4) be at least 18, but not more than 80 years of age; (5) Have a Body Mass Index (BMI)≥19 and ≤45 lb/in$^2$; (6) Have an ASA risk class of I, II, or III according to the American Society of Anesthesiologists; (7) Have the ability to read and understand the Study procedures and the use of the pain scales and have the ability to communicate meaningfully with the Study Investigator and staff; (8) Be free of other physical, mental, or medical conditions which, in the opinion of the Investigator, makes Study participation inadvisable Exclusion Criteria (Screening)

A Subject is NOT eligible for entry if ANY of the following criteria are met: (1) Used opioids or tramadol daily for greater than 7 days prior to Study Medication administration (Subjects who, in the Investigator's opinion have or are developing opioid tolerance are to be excluded); (2) Has been treated with Chapparal, Comfrey, Germander, Gin Bu Huan, Kava, Pennyroyal, Skullcap, St. John's Wort, or Valerian within 14 days prior to surgery; (3) Has significant medical disease(s), laboratory abnormalities or condition(s) that in the Investigator's judgment could compromise the Subject's welfare, ability to communicate with the Study staff, complete Study activities, or would otherwise contraindicate Study participation; (4) Has known hypersensitivity to opioids, acetaminophen, or the inactive ingredients (excipients) of the Study Medication; (5) Has known or suspected history of alcohol or drug abuse or dependence within the previous 2 years; (6) Has impaired liver function, e.g., AST/ALT/bilirubin greater than or equal to 3.0 times the upper limit of normal, active hepatic disease, evidence of clinically significant liver disease, or other condition (e.g., alcoholism, cirrhosis, or hepatitis) that may suggest the potential for an increased susceptibility to hepatic toxicity with Study Medication exposure; (7) Has been treated with monoamine oxidase inhibitors (MAOIs) within 7 days prior to surgery; (8) Has participated in another clinical Study (investigational or marketed product) within 30 days of surgery Post Operative Exclusion Criteria The Subject must not meet any of the following criteria after surgery and prior to randomization to Study Medication: (1) Had any other surgery than the planned laparoscopic surgery or had intra operative or post operative complications which in the view of the Investigator would make Study participation inadvisable; (2) Has taken non steroidal anti-inflammatory drugs (NSAIDs), steroids or MAOIs during the day after surgery. Exceptions: The use of low-dose aspirin, e.g., 81 mg/day, for cardioprophylaxis, and topical or inhaled steroids are acceptable; (3) Had any neuraxial opioids or continuous local anesthetic infusions via percutaneous catheters administered as part of the anesthetic or post operative analgesic management (local anesthetic infiltration of surgical wounds at the time of closure is acceptable if done as a single injection); (4) Had a fever (greater than 38.6° C. or 101.5° F.) requiring treatment.

Postoperative Assessment (POD0)

The Subject will undergo abdominal laparoscopic surgery or other approved surgical procedure as described herein. Details of the surgical procedure(s) will be recorded on the CRF including the type of procedure(s) performed and perioperative medication will be recorded.

Example 4

Phase III, Open-Label, Prospective, Multi-Center, Repeated Dose, Randomized, Multi-Day Safety and Efficacy Study of 650 mg IV Acetaminophen A Phase III, open-label, prospective, multi-center, repeated dose, randomized, multi-day safety and efficacy study was conducted in 213 subjects. The subjects were randomized as follows: 92 subjects to a q6 group (1 g of IV acetaminophen every 6 hours), 91 subjects to a q4 group (650 mg of IV acetaminophen every 4 hours), and 28 subjects to a standard of care control group, which could include oral acetaminophen, but no IV acetaminophen. Subjects who completed 5 days of study treatment included 63 in the q6 group, 59 in the q4 group and 26 in the control group. The primary endpoint was an assessment of safety using spontaneous adverse event reporting and daily liver enzymes. Efficacy evaluations were also performed.

Inclusion Criteria (Screening)

To be eligible for entry into the Study, Subjects had to meet all the following criteria: (1) Provide written informed consent prior to participation in the Study; (2) Be at least 18 years of age and weigh at least 41 kg; (3) Be anticipated by the Investigator to require multi-day (target is five days) use of IV treatment either because of: (a) having a "nothing by mouth" (NPO) status, (b) having a medical condition that makes oral intake difficult, or (c) having a medical condition that requires IV treatment; (4) Be willing to undergo 5 days of treatment with IV acetaminophen for the treatment of pain or fever (defined as a core temperature ≥38° C.). Subjects had a slightly less than 15% chance (one in seven) of being assigned to the Control Group and receiving standard of care treatment, but no IV APAP; (5) Have the ability to read and understand the Study procedures and have the ability to communicate meaningfully with the Study Investigator and staff, and (6) If a female of child bearing potential, have a negative pregnancy test within 48 hours of randomization.

Exclusion Criteria (Screening)

A Subject was not eligible for entry if any of the following criteria were met: (1) Had a significant medical disease, laboratory abnormality or condition that, in the Investigator's judgment, could compromise the Subject's welfare or would otherwise contraindicate Study participation; (2) Was expected to have difficulty in communicating with the Study staff or completing Study requirements (including follow up visits); (3) Had known hypersensitivity to acetaminophen or the inactive ingredients (excipients) of IV acetaminophen or any contraindication to receiving acetaminophen; (4) Had impaired liver function, e.g., ALT greater than or equal to 3 times the upper limit of normal (ULN), bilirubin greater than or equal to 3 times ULN, known active hepatic disease (e.g., hepatitis), evidence of clinically significant chronic liver disease or other condition affecting the liver (e.g., alcoholism as defined by DSM-IV, cirrhosis or chronic hepatitis); or (5) Had participated in an interventional clinical Study (investigational or marketed product) within 30 days of Study entry.

Efficacy Analysis

All analyses of efficacy were conducted on the modified intent-to-treat population separately for the two indications (acute pain and fever). Subjects' Global Evaluations were summarized descriptively (m, mean, SD, median, minimum, and maximum) by treatment group for each study day and for overall assessments. Summary statistics were also provided for each site.

Comparisons of efficacy endpoints between the following pairs of treatment groups were investigated using two-sided tests at the 5% level of significance:

IV acetaminophen 1 g versus IV acetaminophen 650 mg
IV acetaminophen 1 g versus standard of care treatment
IV acetaminophen 650 mg versus standard of care treatment A one-way analysis of variance (ANOVA) model with treatment group as the factor was used to test the treatment difference between these pairs. All groups were included in this analysis model. The p-values from the ANOVA model were presented along with the summary statistics.

Safety Analyses

All analyses of safety were conducted on the safety population.

Percentage of subjects withdrawn due to adverse event, percentage of subjects with adverse events (AEs) or serious adverse events (SAEs), and percentage of subjects with clinically meaningful changes in laboratory parameters were summarized.

All adverse events and serious adverse events were coded according to the Medical Dictionary for Regulatory Activities (MedDRA), Version 10.0. Additional analyses included displays of the number of subjects reporting at least one AE (incidence table), total number of episodes of each AE by body system and by severity, total number of episodes of each AE by body system, and by attribution. Liver function test abnormalities were graded using the Common Terminology Criteria for Adverse Events.

For each clinical laboratory parameter, descriptive statistics (m, mean, standard deviation, median, and range) were tabulated for baseline and final values. Change from baseline was tabulated for those subjects who had both baseline and final values. Liver function tests were also evaluated using values that were normalized to the upper limit of normal values for the local laboratory.

A shift table was prepared to present the shift in baseline clinical laboratory values that were clinically relevantly high or low at baseline and/or final measurement.

Descriptive statistics (m, mean, standard deviation, median, and range) were tabulated for changes in vital signs from baseline to final measurement.

Results

Disposition of Subjects

A total of 257 subjects were screened for study enrollment. Of the total screened, 44 were screen failures, and 213 were enrolled and randomized: 92 subjects in the q6 group, 91 subjects in the q4 group, and 28 subjects in the control group.

Subjects who completed 5 days of study treatment included 63 in the q6 group, 59 in the q4 group and 26 in the control group.

Subjects in the q4h group and q6h group were considered to be a Study Treatment Discontinuation/Early Termination if they received at least one dose of IV acetaminophen and discontinued study participation prior to completion of Day 5 treatments. Subjects in the control group were considered to be a Study Treatment Discontinuation/Early Termination if they discontinued at any time after T0, but prior to completion of Day 5 standard of care treatments.

Subjects who received at least one dose of IV acetaminophen and discontinued study participation prior to completing Day 5 treatments, but returned for the Last Study Visit were considered as "Partial Treatment Completers". Similarly, subjects in the control group who discontinued study participation prior to completing Day 5 standard of care treatments, but returned for the Last Study Visit were considered as "Partial Treatment Completers".

Subjects who completed Day 5 treatments (IV acetaminophen or standard of care) and procedures were characterized as a "Treatment Completer". A Treatment Completer who elected to discontinue study participation prior to the Last Study Visit was characterized as a Treatment Completer Early Termination.

Safety Outcome

There were no clinically relevant differences between the treatment groups in the frequency of serious, severe, related, or overall treatment emergent adverse events (TEAEs). In fact, most TEAEs were assessed by the Investigator to be mild or moderate in severity. The frequency of liver enzyme elevations seen in the treatment groups was comparable. More specifically, with regard to the hepatic transaminases alanine aminotransferase and aspartate aminotransferase, the frequency and severity of the elevations were comparable between the treatment groups. There were no clinically relevant differences between the treatment groups regarding laboratory assessments, vital signs, or physical examinations. Thus, based on these data, intravenous acetaminophen in both active treatment groups (i.e., 650 mg and 1000 mg dose groups) was well tolerated.

Efficacy Outcome

The modified intent-to-treat population was used for all analyses of efficacy: Subject Global Evaluations (rating of study treatments and rating of satisfaction with side effects related to study treatments) provided as a daily lookback (days 2 through 5) and overall evaluation (overall treatment period lookback) using a 4 point categorical rating scale (0=poor, 1=fair, 2=good, 3=excellent). A one-way ANOVA model with treatment group as the factor was used to test the treatment difference between each treatment pair:

IV acetaminophen 1 g q6h versus IV acetaminophen 650 mg q4h

IV acetaminophen 1 g q6h versus standard of care treatment (Control)

IV acetaminophen 650 mg q4h versus standard of care treatment (Control)

All endpoints were tested at the 0.05 significance level (two-sided).

The IV acetaminophen 650 mg q4h group relative to the control group produced statistically significantly better satisfaction ratings for the Subject Global Assessments rating the level of satisfaction with the side effects related to study treatments the on the day 5 (mean rating 2.4 vs. 2.0, p=0.0167) and at the end of day 5 prior to discharge (mean rating 2.4 vs. 2.0, p=0.0129) 24 h look back assessments. On day 4, the satisfaction rating showed a trend to significance (mean rating 2.5 vs. 2.2, p=0.1162). With respect to the Subject Global Assessments rating the level of satisfaction with the study treatments, there were no statistically significant differences between the IV acetaminophen 650 mg q6h group and control group at any of the assessment points. For the both of the Subject Global Assessments rating either the level of satisfaction with the study treatments or the level of satisfaction with the side effects related to study treatments, there was no statistically significant differences between the two active treatment groups with respect to the daily 24 h lookback assessments on day 2, day 3, day 4, day 5, or at the end of day 5 prior to discharge; nor was there a statistically significant difference on the overall assessment at the Study Completion Visit.

The IV acetaminophen 1 g q6h group produced statistically significantly better satisfaction ratings for the Subject Global Assessments rating the level of satisfaction with the side effects related to study treatments on day 5 (mean rating 2.4 vs. 2.0, p=0.0062) and at the end of day 5 prior to discharge (mean rating 2.5 vs. 2.0, p=0.0073) 24 h lookback assessments compared to the control group. On day 4, the satisfaction rating showed a trend to significance (mean rating 2.5 vs. 2.2, p=0.0744). With respect to the Subject Global Assessments rating the level of satisfaction with the study treatments, there were no statistically significant differences between the IV acetaminophen 1 g q6h group and control group at any of the assessment points.

Statistically significant differences were observed for both active treatment groups versus the control group in the Subject Global Assessments rating the level of Satisfaction with the side effects related to study treatments on the day 5 and on the end of day 5 prior to discharge daily 24 h lookback assessments. Thus, these data suggest that the IV acetaminophen 1 g q6h and 650 mg q4h groups were efficacious and provided comparable efficacy based upon the global satisfaction ratings.

Many modifications, equivalents, and variations of the present invention are possible in light of the above teachings, therefore, it is to be understood that within the scope of the appended claims, the invention may be practiced other than as specifically described.

What is claimed is:

1. A method for the treatment of pain or fever in an adult human or an adolescent human subject weighing at least 50 kg, in need thereof, comprising administering to the subject, by an intravenous route of administration, a therapeutically effective amount of a pharmaceutical composition comprising about 550 mg to about 800 mg of acetaminophen; and repeating said administration at least once at an interval of about 3 to about 5 hours.

2. The method of claim 1, wherein the subject receives a total of about 3 to about 5 grams of acetaminophen in a period of twenty four hours.

3. The method of claim 2, wherein the pharmaceutical composition is administered at least six times in a period of twenty four hours.

4. The method of claim 1, wherein the pharmaceutical composition comprises at least one antioxidant.

5. The method of claim 4, wherein the at least one antioxidant is selected from the group consisting of cysteine hydrochloride monohydrate, thiolyglycolic acid, thiolacetic acid, dithiothreitol, reduced glutathione, thiourea, a-thioglycerol, cysteine, aceticysteine, mercaptoethane sulfonic acid, ascorbic acid, ascorbic acid derivatives, an organic compound having at least one thiol, an alkyl polyhydroxylated compound, a cycloalkyl polyhydroxylated compound, and mixtures thereof.

6. The method of claim 5, wherein the at least one antioxidant comprises cysteine hydrochloride monohydrate.

7. The method of claim 1, further comprising a buffering agent.

8. The method of claim 7, wherein the buffering agent comprises disodium phosphate dehydrate.

9. The method of claim 1, wherein the pharmaceutical composition has a pH between about 4 to about 8.

10. The method of claim 9, wherein the pharmaceutical composition has a pH of between about 5 and about 6.

11. The method of claim 1, wherein the pharmaceutical composition has an osmolality of between about 200 mOsm/L to about 400 mOsm/L.

12. The pharmaceutical composition of claim 11, wherein the acetaminophen is present in the composition in an amount of about 600 mg to about 700 mg.

13. The method of claim 1, wherein the pharmaceutical composition further comprises an isotonicity agent.

14. The method of claim 13, wherein the isotonicity agent is dextrose, mannitol, or lactose.

15. The method of claim 14, wherein the isotonicity agent is mannitol.

16. The method of claim 1, further comprising EDTA.

17. The method of claim 1, wherein the pharmaceutical composition further comprises at least one analgesic agent other than acetaminophen.

18. The method of claim 17, wherein the at least one analgesic agent other than acetaminophen comprises an anilide, an opioid, an NSAID, a cannabinoid, a pyrazalone, or a barbiturate.

19. The method of claim 18, wherein the at least one analgesic agent other than acetaminophen comprises an opioid.

20. The method of claim 1, wherein the subject is suffering from a fever.

21. The method of claim 1, wherein the subject is unconscious, sedated, fasting, nauseous, or unable to be administered a pharmaceutical composition by an oral route.

22. The method of claim 1, wherein the pharmaceutical composition is administered after a surgical intervention on the subject.

23. The method of claim 1, wherein the pharmaceutical composition is administered within 3 hours of a surgical intervention on the subject.

24. The method of claim 23, wherein the pharmaceutical composition is administered within 1 hour of a surgical intervention on the subject.

25. The method of claim 1, wherein the pharmaceutical composition is administered postoperatively.

26. The method of claim 1, further comprising administering to the subject at least one analgesic agent other than acetaminophen.

27. The method of claim 26, wherein the at least one analgesic agent other than acetaminophen comprises an anilide, an opioid, an NSAID, a cannabinoid, a pyrazalone, or a barbiturate.

28. The method of claim 1, wherein the subject is suffering from an infection.

29. A method for reducing pain or fever in an adult human or an adolescent human subject weighing at least 50 kg, in need thereof, comprising administering to the subject, by an intravenous route of administration, a therapeutically effective amount of a pharmaceutical composition in solution comprising: about 600 mg to about 700 mg of acetaminophen, cysteine hydrochloride monohydrate, disodium phosphate dehydrate, and mannitol, wherein the solution has a pH of about 5 to about 6, and an osmolality of about 200-400 mOsm/L; and repeating said administration at least once at an interval of about 3 to about 5 hours.

30. The method of claim 29, wherein the pharmaceutical composition has an acetaminophen concentration of about 0.5% (w/v) to about 10% (w/v).

31. The method of claim 30, wherein the acetaminophen concentration is about 1% (w/v).

32. The method of claim 29, wherein the pharmaceutical composition further comprises EDTA.

33. The method of claim 29, wherein the subject is suffering from postoperative pain.

34. The method of claim 1, wherein the level of pain the subject is suffering from is reduced.

35. The method of claim 1, wherein the pharmaceutical composition is administered as a pretreatment.

36. The method of claim 29, wherein the administered dose of acetaminophen is 650 mg, and further comprising repeating intravenous administration of 650 mg acetaminophen at least once at an interval of about 3 hours to about 5 hours.

37. The method of claim 36, wherein the interval is about 4 hours.

38. The method of claim 1, further comprising repeating intravenous administration of about 600 mg to about 700 mg acetaminophen at least once at an interval of about 3 hours to about 5 hours.

39. The method of claim 1, wherein the administered dose of acetaminophen is 650 mg, and further comprising repeating intravenous administration of 650 mg acetaminophen at least once at an interval of about 3 hours to about 5 hours.

40. The method of claim 29, wherein the interval is about 4 hours.

41. The method of claim 1, wherein the composition may be administered to the subject without dilution.

42. The method of claim 1, wherein the composition is a sterile solution that is ready for direct administration to the subject.

43. The method of claim 1, wherein the pharmaceutical composition is a lyophilized powder.

44. The method of claim 43, wherein the lyophilized powder must be reconstituted in solution prior to administration.

45. The method of claim 1, wherein the pharmaceutical composition is intravenously administered to the subject over about 5 minutes to about 30 minutes.

46. The method of claim 45, wherein the pharmaceutical composition is intravenously administered to the subject over about 15 minutes.

47. The method of claim 1, wherein the subject is administered less than 4 grams of acetaminophen over a twenty-four hour period.

48. A method of treating pain in a human subject weighing at least 50 kg comprising:
    administering to the subject a therapeutically effective amount of a pharmaceutical composition comprising about 600 mg to about 700 mg of acetaminophen; and
    repeating said administration at least about once every 4 hours;
    wherein the composition is administered to the subject as a 15-minute intravenous infusion, and
    wherein the subject is administered less than 4 grams of acetaminophen over a 24-hour period.

49. The method of claim 48, wherein the composition comprises about 650 mg of acetaminophen.

50. The method of claim 48, wherein the composition is administered to the subject at least six times in a period of 24 hours.

51. The method of claim 48, wherein the composition is administered to the subject at least seven times in a period of 24 hours.

52. The method of claim 48, wherein the composition is administered to the subject at least eight times in a period of 24 hours.

53. The method of claim 48, wherein the composition may be administered to the subject without dilution.

54. The method of claim 48, wherein the composition is a sterile solution that is ready for subject administration.

55. The method of claim 48, wherein the composition is a lyophilized powder.

56. The method of claim 55, wherein the lyophilized powder must be reconstituted in solution prior to subject administration.

57. The method of claim 48, wherein the composition may be stored at ambient temperature for two years prior to use.

58. The method of claim 57, wherein the ambient temperature is less than 30 degrees Celsius.

59. The method of claim 48, wherein the composition further comprises a buffer in an amount of about 0.1% to about 0.7%.

60. The method of claim 48, wherein the composition further comprises a buffer in an amount of about 0.2% to about 0.3%.

61. The method of claim 48, wherein the composition further comprises a buffer in an amount of about 0.05% to about 2.0%.

62. The method of claim 48, wherein the composition further comprises at least one buffering agent.

63. The method of claim 62, wherein the at least one buffering agent is selected from the group consisting of a pharmaceutically acceptable salt or acid of citrate, phosphate, acetate, glutamate, tartrate, benzoate, lactate, histidine or other amino acids, gluconate, malate, succinate, formate, propionate, carbonate, or any combination thereof.

64. The method of claim 63, wherein the at least one buffering agent is disodium phosphate dehydrate.

65. The method of claim 48, wherein the pharmaceutical composition has a pH between about 4 to about 8.

66. The method of claim 48, wherein the pharmaceutical composition has a pH of between about 5 and about 6.

67. The method of claim 48, wherein the composition further comprises an antioxidant in an amount of about 0.3% to about 1.0%.

68. The method of claim 48, wherein the composition further comprises an antioxidant in an amount of about 0.5%.

69. The method of claim 48, wherein the composition further comprises at least one antioxidant.

70. The method of claim 69, wherein the at least one antioxidant is selected from the group consisting of cysteine hydrochloride monohydrate, thiolyglycolic acid, thiolactic acid, dithiothreitol, reduced glutathione, thiourea, a-thioglycerol, cysteine, aceticysteine, mannitol, mercaptoethane sulfonic acid, ascorbic acid, ascorbic acid derivatives, an organic compound having at least one thiol, an alkyl polyhydroxylated compound, a cycloalkyl polyhydroxylated compound, and mixtures thereof.

71. The method of claim 70, wherein the at least one antioxidant is cysteine hydrochloride monohydrate.

72. The method of claim 70, wherein the at least one antioxidant is mannitol.

73. The method of claim 48, wherein the composition further comprises an isotonicity agent in an amount of about 65% to about 85%.

74. The method of claim 48, wherein the composition further comprises at least one isotonicity agent.

75. The method of claim 74, wherein the at least one isotonicity agent is selected from the group consisting of mannitol, sorbitol, glycerol, sucrose, glucose, dextrose, levulose, fructose, lactose, polyethylene glycols 400 to 4000, phosphates, sodium chloride, potassium chloride, calcium chloride, calcium gluconoglucoheptonate, dimethyl sulfone, and combinations thereof.

76. The method of claim 75, wherein the at least one isotonicity agent is mannitol.

77. The method of claim 48, wherein the composition has an osmolality of between about 200 mOsm/L to about 400 mOsm/L.

78. The method of claim 48, wherein the composition comprises 650 mg of acetaminophen, and wherein the subject is administered the composition every four hours in a twenty-four hour period.

79. A method of reducing fever in a human subject weighing at least 50 kg comprising:
administering to the subject a therapeutically effective amount of a pharmaceutical composition comprising about 600 mg to about 700 mg of acetaminophen; and
repeating said administration at least about once every 4 hours;
wherein the composition is administered to the subject as a 15-minute intravenous infusion, and
wherein the subject is administered less than 4 grams of acetaminophen over a twenty-four hour period.

80. The method of claim 79, wherein the composition comprises about 650 mg of acetaminophen.

81. The method of claim 79, wherein the composition is administered to the subject at least six times in a period of 24 hours.

82. The method of claim 79, wherein the composition is administered to the subject at least seven times in a period of 24 hours.

83. The method of claim 79, wherein the composition is administered to the subject at least eight times in a period of 24 hours.

84. The method of claim 79, wherein the composition may be administered to the subject without dilution.

85. The method of claim 79, wherein the composition is a sterile solution that is ready for subject administration.

86. The method of claim 79, wherein the composition is a lyophilized powder.

87. The method of claim 86, wherein the lyophilized powder must be reconstituted in solution prior to administration.

88. The method of claim 79, wherein the composition may be stored at ambient temperature for two years prior to use.

89. The method of claim 88, wherein the ambient temperature is less than 30 degrees Celsius.

90. The method of claim 79, wherein the composition further comprises a buffer in an amount of about 0.1% to about 0.7%.

91. The method of claim 79, wherein the composition further comprises a buffer in an amount of about 0.2% to about 0.3%.

92. The method of claim 79, wherein the composition further comprises a buffer in an amount of about 0.05% to about 2.0%.

93. The method of claim 79, wherein the composition further comprises at least one buffering agent.

94. The method of claim 93, wherein the at least one buffering agent is selected from the group consisting of a pharmaceutically acceptable salt or acid of citrate, phosphate, acetate, glutamate, tartrate, benzoate, lactate, histidine or other amino acids, gluconate, malate, succinate, formate, propionate, carbonate, or any combination thereof.

95. The method of claim 94, wherein the at least one buffering agent is disodium phosphate dehydrate.

96. The method of claim 79, wherein the pharmaceutical composition has a pH between about 4 to about 8.

97. The method of claim 79, wherein the pharmaceutical composition has a pH of between about 5 and about 6.

98. The method of claim 79, wherein the composition further comprises an antioxidant in an amount of about 0.3% to about 1.0%.

99. The method of claim 79, wherein the composition further comprises an antioxidant in an amount of about 0.5%.

100. The method of claim 79, wherein the composition further comprises at least one antioxidant.

101. The method of claim 100, wherein the at least one antioxidant is selected from the group consisting of cysteine hydrochloride monohydrate, thiolyglycolic acid, thiolacetic acid, dithiothreitol, reduced glutathione, thiourea, a-thioglycerol, cysteine, aceticysteine, mannitol, mercaptoethane sulfonic acid, ascorbic acid, ascorbic acid derivatives, an organic compound having at least one thiol, an alkyl polyhydroxylated compound, a cycloalkyl polyhydroxylated compound, and mixtures thereof.

102. The method of claim 101, wherein the at least one antioxidant is cysteine hydrochloride monohydrate.

103. The method of claim 101, wherein the at least one antioxidant is mannitol.

104. The method of claim 79, wherein the composition further comprises an isotonicity agent in an amount of about 65% to about 85%.

105. The method of claim 79, wherein the composition further comprises at least one isotonicity agent.

106. The method of claim 105, wherein the at least one isotonicity agent is selected from the group consisting of mannitol, sorbitol, glycerol, sucrose, glucose, dextrose, levulose, fructose, lactose, polyethylene glycols 400 to 4000, phosphates, sodium chloride, potassium chloride, calcium chloride, calcium gluconoglucoheptonate, dimethyl sulfone, and combinations thereof.

107. The method of claim 106, wherein the at least one isotonicity agent is mannitol.

108. The method of claim 79, wherein the composition has an osmolality of between about 200 mOsm/L to about 400 mOsm/L.

109. The method of claim 79, wherein the pharmaceutical composition comprises 650 mg of acetaminophen, and wherein the subject is administered the composition every four hours in a twenty-four hour period.

* * * * *